United States Patent [19]

Rael et al.

[11] Patent Number: 5,053,492

[45] Date of Patent: Oct. 1, 1991

[54] IMMUNOPURIFICATION USING MONOCLONAL ANTIBODIES TO MOJAVE TOXIN

[75] Inventors: Eppie D. Rael; Richard J. Salo, both of El Paso, Tex.

[73] Assignee: Board of Regents, The University of Texas System, Austin, Tex.

[21] Appl. No.: 893,919

[22] Filed: Aug. 7, 1986

[51] Int. Cl.$^5$ .................. A61K 39/395; C07K 15/28; C07K 3/20

[52] U.S. Cl. .................................. 530/387; 530/388; 530/391; 530/392; 530/393; 530/413; 530/856; 435/70.21; 435/172.2; 435/240.27; 935/108; 935/110; 436/548

[58] Field of Search ............... 435/240.27, 172.2, 948, 435/198, 815, 68; 530/387, 413, 856, 391, 392, 393; 935/108, 110; 436/548

[56] References Cited

PUBLICATIONS

Dialog Search Report.
Henderson, J. T et al. (I), "Antigenic relatedness of crotalid venoms: the basic subunit of mojave toxin", First American Symposium on Animal, Plant and Microbial Toxins Held by the International Society on Toxicology (American Section), Stillwater, Okla., U.S.A., May 23–25, 1984, Toxicon, 23(1):23, 1985.
Henderson, J. T. et al. (II), "Antigenic Relationships Between Mojave Toxin Subunits, Mojave Toxin and Some Crotalid Venoms," Toxicon 24(5):473–479, 1986.
Cate, R. L. et al., "Purification and Characterization of Mojave (Crotalus scutalatus scutalatus) Toxin and its Subunits," Arch. Biochem. Biophys. 189(2): Aug., 1978, pp. 397–408.
Perez et al., "Production of a Monoclonal Antibody Against Hemorrhagic Activity of Crotalus Atrox (Western Diamondback Rattlesnake) Venom," Toxicon 22(6): 967–973, 1984.
Goding, J. W., Monoclonal Antibodies: Principles and Practice, Academic Press, Inc., Orlando, 1983, pp. 188–207.
Chandler, H. M. et al., "A new enzyme immunoassay system suitable for field use and its application in a snake venom detection kit," Clinica Chimica Acta 121: 225–230, 1982.
Rael, et al., (1986), Toxicon, 24:661.
Chambers, et al., (1986), Brain Res. Bull., 16:639.
Rael, et al., (1986), Abstract presented at 2nd American Symposium on Animal, Plant and Microbial Toxins, May 20–23, 1986.
Huang, et al. (1985), Toxicon, 23:30.
Zeppeda, et al., (1985), Comp. Biochem. Physiol., 818:319.
Rael, et al. (1984), Toxicon, 22:980.
Perez, et al. (1984), Toxicon, 22:907.
Russo, et al., (1983), Toxicon, 21:433.
Theakston, (1983), Toxicon, 21:341.
Sullivan, et al. (1982), Proc. West. Pharmacol. Soc. 25:185.

Primary Examiner—Margaret Moskowitz
Assistant Examiner—Jeff Kushan
Attorney, Agent, or Firm—Arnold, White & Durkee

[57] ABSTRACT

Monoclonal antibodies to Mojave toxin and use for isolation of cross-reacting proteins in Crotalus venoms are disclosed. Hybridomas secreting monoclonal antibodies against Mojave toxin were established. The antibodies were used for identifying cross-reacting proteins in individual *C. s. scutulatus* and other Crotalus venoms and to isolate Mojave toxin. The antibodies recognized five bands with a pI range from 5.1 to 6.1 in immunoblots of electrofocused crude venom and Mojave toxin purified by immunoaffinity chromatography. The specificity of the antibodies was for the basic subunit of the toxin which resolved into four bands of pI between 9.3 and 9.6. Individual *C. s. scutulatus* venoms of snakes from Texas and southern Arizona had multiple bands with pI's ranging from 4.9 to 6.3. Cross-reacting proteins were also recognized by antibodies in the electrophoresed venoms of *C. basiliscus, C. d. durissus, C. d. terrificus, C. h. horridus,* and *C. v. concolor,* and may be isolated by immunoaffinity chromatography with the monoclonal antibodies.

9 Claims, No Drawings

IMMUNOPURIFICATION USING MONOCLONAL ANTIBODIES TO MOJAVE TOXIN

BACKGROUND OF THE INVENTION

The government may own certain rights in the present invention pursuant to NIH grant GRS 5-S06-RR08012-14.

1. Field of the Invention

The present invention is directed to monoclonal antibodies to Mojave toxin which are useful in the isolation of Mojave toxin and immunologically related toxins found in the Crotalus genus of snakes.

2. Description of the Related Art

Mojave toxin, from the venom of *Crotalus scutulatus scutulatus*, the Mojave rattlesnake, is a presynaptic neurotoxin capable of blockade of acetylcholine release and myotoxicity. It is a protein complex of pI 5.5, composed of one basic subunit possessing phospholipase activity, of 14,673 Daltons and pI of 9.3 and an acidic subunit of 9,593 Daltons and pI of 3.6. The subunits are associated through noncovalent bonding and their separation results in loss of toxicity, but full toxic potency is generated after reconstitution. The basic component has phospholipase activity but no enzymatic activity has yet been shown for the acidic subunit.

In depth immunological studies of the Crotalus toxins are important to an understanding of the physiological phenomena associated with snake bit toxicity. However, such studies have been hampered in the past due to an unavailability of monovalent antisera which are specific for various components which make up the venom.

The availability of monospecific antibodies which recognize individual toxin components could serve numerous useful purposes in the area of snake venom study. For example, snake venoms are the single most important source of cell destroying toxins found in nature. Whereas plant and bacterial toxins, for example, ricin, abrin and diptheria toxin, have been used in the field of antitumor research to formulate tumor-specific immunotoxins, these toxins have the disadvantage of exerting their cytotoxic activity intracellularly. Thus, such antibody-toxin conjugates must be internalized by the target tumor cell before the toxin will exert its cell killing effect. However, Mojave toxin, and related venom toxins, exert their toxic activity at the cell surface level. Therefore, it is contemplated by the present inventors that immunotoxins derived from the use of such cell-surface active snake venom toxins will provide a great benefit in the field of antitumor immunotoxins. The ability to isolate highly purified Mojave toxin for such uses could be achieved through the development of highly specific monoclonal antibodies which are capable of reacting with Mojave toxin, or selected subunits thereof.

The ability to specifically generate and isolate monovalent antibodies to toxin components of snake venoms would further provide the possibility of developing highly active antivenin. Antivenins currently in use must be given in very large quantities, sometimes in the amount of one-tenth of the patient's total blood volume. However, the availability of highly specific monoclonal antitoxins would provide a basis for formulating monoclonal antivenins with a much higher antibody titer which could be administered to patients in much reduced volumes.

Perhaps more importantly from the stand point of the present invention, there is currently no available clinical test to determine the venom type which a rattlesnake bit victim has received. Rattlesnakes can be classified as producing either type A or type B venom, these venoms being distinguishable on the basis of whether they include Mojave toxin (type A venoms) or not. The presence of Mojave toxin in type A venoms make this venom a much more serious clinical situation and the ability to quickly identify type A snake bite victims would be of great clinical utility. Thus, the availability of monoclonal antibodies which are specific for Mojave toxin would provide the basis for formulating such a clinical test.

SUMMARY OF THE INVENTION

Accordingly, the present invention provides a monoclonal antibody having the capability of specifically identifying and binding to Mojave toxin. Mojave toxin monoclonal antibodies made in accordance with the present invention have the ability of recognizing and binding to not only the Mojave toxin itself but, in addition, such antibodies will recognize and bind to immunologically cross-reactive toxin components of venoms found in various other snakes of the Crotalus genus. Immunologically cross-reacting snake venoms of this genus include, but are not limited to, snake venoms from the species of *C. s. scutulatus, C. d. durissus, C. d. terrificus, C. h. horridus, C. v. concolor*.

Monoclonal antibodies made to Mojave toxin have the ability of forming an antibody/antigen complex with Mojave toxin, and immunologically related, toxins. Therefore, monoclonal antibodies of the present invention are useful in isolating and identifying toxin components of these snake species.

In one embodiment of the present invention, monoclonal antibodies are provided which react specifically with the basic subunit of Mojave toxin. This subunit has a molecular weight of approximately 14,600 Daltons and a pI of approximately 9.3. This basic component has phospholipase activity, and therefore may be referred to alternatively as the phospholipase component. However, there are other phospholipase activities associated with rattlesnake venom, particularly phospholipase $A_2$, which do not cross-react immunologically with the basic subunit of Mojave toxin.

Compositions which include monoclonal antibodies of the present invention may be prepared by first fusing spleen cells of a rodent with myeloma cells from the same rodent species, wherein the rodent providing the spleen cells has been immunized with Mojave toxin, or a selected subunit thereof. Although the rodent species utilized is preferably a mouse, rats may be used as well for the development of a stable hybrid continuous cell line. Typically, sublethal doses of a crude Mojave toxin preparation is injected into the rodent to achieve an immunological reaction to this immunogen. After an immunological reaction has been achieved, the spleen cells of the immunized rodent are isolated and fused to myeloma cells using one of various procedures known to those skilled in the art. In a preferred embodiment, fusions are performed using polyethylene glycol. However, other fusion methods are known, for example, the use of Sendai virus. Moreover, numerous myeloma cell types are known in the art to be useful in the preparation of hybrid continuous cell lines, the NS-1 myeloma is preferably used where mouse is the rodent selected.

After a fusion of spleen cells to myeloma cells has been achieved, the fusion mixture is cultured in a selective medium which selects for the fused cells while allowing nonfused cells to die. A typical selection medium known to be useful in the isolation of NS-1 myeloma-fused cells is the HAT medium which includes hypoxanthine, aminopterin and thymidine. The formulation and use of the HAT selection medium is well known to those skilled in the art.

During incubation of the fused cells in the selective medium, cell culture fluids are analyzed for antibodies which are capable of immunologically reacting with Mojave toxin. Numerous methods are known in the art for achieving such an immunological screening, for example, ELISA, radioimmunoassay and related immunoassays. The present inventors have found that the immunodot assay is particularly convenient for achieving an immunological screening. Once hybridoma clones have been identified which cross-react immunologically with the Mojave toxin, such clone may be further cultured to produce substantially pure clones which produce quantities of the monoclonal antibody for further characterization, study and use.

In addition, the present invention provides a method for isolating Mojave toxin and snake venom toxins which are antigenically cross-reactive with Mojave toxin. This method includes preparing an immunoadsorbent material having attached thereto an antibody to Mojave toxin, or a selected subunit thereof. Numerous immunoadsorbent materials are known to those skilled in the art and include, for example, Affi-Gel, CN-Sepharose, protein A-Sepharose, and numerous other well known immunoadsorbent techniques. All such techniques are applicable to the present invention and should be useful in the isolation of the immuno cross-reactive toxin species (for a more complete listing, See *Monoclonal Hybridoma Antibodies: Techniques and Applications*, John G. Hurrell, ed., CRC Press, 1982, incorporated herein by reference).

Once an immunoadsorbent material is selected, the anti-toxin antibody is attached thereto in the manner appropriate for the particular immunoadsorbent material selected. The snake venom having the particular snake venom toxin to be isolated is then brought into contact with the immunoadsorbent material in a manner which will promote the formation of an antigen/antibody complex. After this mixture is washed sufficiently to remove non-immunoreacting substances, for example, non-cross-reacting proteins, the specifically immuno-bound toxin may be eluted in a purified form to provide the purified toxin. The particular elution technique will depend on the particular antigen, antibody and adsorbent material selected, however, such elution techniques will be well within the skill of the art.

Moreover, kits may be provided in accordance with the present invention to allow for a clinical detection of Mojave, and related toxins, in a biologic sample. Such kits would include monoclonal antibodies having specificity for Mojave toxin, or immunologically related toxins, in combination with an immunodetection reagent. An immunodetection reagent is defined as any reagent for detecting or quantifying the formation of antibody/antigen complexes. Typical immunodetection reagents include the use of radiolabeled or enzyme-labeled antigens or antibodies. Techniques which incorporate labeled antibodies include, for example, RIA (radioimmunoassay) and ELISA (enzyme-linked immuno assay). However, numerous other techniques are known which may be employed in immunodetection kits in accordance with the present invention. Patents which teach suitable techniques include, for example, U.S. Pat. Nos. 4,446,232; 4,407,943; 4,399,229; and 4,454,233.

Thus, a typical Mojave toxin detection kit based on the ELISA technique could include the anti-Mojave toxin monoclonal antibody and a second "immunodetection" antibody capable of specifically immunoreacting with the anti-Mojave toxin antibody. The second antibody would have a color-generating enzymatic activity associated with it, for example, an attached peroxidase molecule. When a second "immunodetection" antibody is employed in this fashion, one will generally first form an immunocomplex between the biologic sample to be tested, for example, serum, plasma, urine or tissue samples, and the anti-Mojave toxin antibody. After forming such an immunocomplex, the immunodetection antibody is added to react quantitatively with toxin-bound Mojave antibody. This complex formation is then quantitated through the colorimetric peroxidase assay.

As alternative to using the above double-antibody technique, one may incorporate the enzyme or radioligand directly onto the anti-Mojave antibody, and quantification made directly with the use of this directly labeled antibody.

The foregoing type of kit and method is well known and can be viewed generally as including the steps of obtaining a biologic sample from a snake bite victim, contacting the biologic sample with anti-Mojave toxin monoclonal antibody under conditions which will promote the formation of antibody/antigen complexes and detecting the formation of a specific immunologic reaction between the monoclonal antibody and the sample.

DESCRIPTION OF THE PREFERRED EMBODIMENTS

Mojave toxin, from the venom of *Crotalus scutulatus scutulatus*, the Mojave rattlesnake, is a presynaptic neurotoxin capable of blocking the release of acetylcholine. This toxin also exerts a profound myotoxicity. It is a protein complex having an overall pI of 5.5, which is composed of one basic subunit with a molecular weight of approximately 14,600 Daltons and a pI of about 9.3, and an acidic subunit of about 9,600 Daltons and pI of approximately 3.6. The two subunits are associated through non-covalent bonding and separation of the subunits results in a loss of toxicity. However, full toxic potency is generated upon reconstitution. Whereas the basic subunit has phospholipase activity, no enzymatic activity has yet been demonstrated for the acidic subunit.

In accordance with a general aspect of the present invention, monoclonal antibodies to Mojave toxin are prepared by first challenging an immuno competent rodent with a venom which contains the toxin. Typically, the species of choice to provide the venom is *C. s. scutulatus*, otherwise referred to as the Mojave rattlesnake. The Mojave rattlesnake is preferred in that the venom of this snake, type A venom, is particularly rich in Mojave toxin. For example, the mouse i.p. $LD_{50}$ for type A venoms is generally approximately 0.28 mg/kg. In contrast, type B venoms, in which Mojave toxin is absent or low in concentrations, exhibits a typical $LD_{50}$ in mice of 3.33 mg/kg. Certain of the type B venomous rattlesnakes may have a sufficient Mojave toxin concentration to elicit a Mojave toxin specific immune response in immunized rodents. However, the type A venomous rattlesnake is a preferred source. Alternatively, venoms which contain Mojave toxin may be obtained from commercial sources (Sigma Chemical Co., St. Louis, MO).

The type of rodent used for immunologic challenge is basically a matter of choice. Due to the ready availability of the murine NS-1 myeloma, one may preferably wish to utilize mice for the development of the immune response. However, as previously mentioned, the rat system represents a suitable alternative to the murine system.

The following example details the particular methodology utilized by the present inventors in developing a hybrid continuous cell line which secretes Mojave toxin-specific monoclonal antibodies. However, as those of skill in the art will appreciate, modifications may be incorporated in the following technique without departing from the intended scope of the present invention.

EXAMPLE I

Generation of Monoclonal Antibodies To Mojave Toxin a. Venom

Venoms were purchased from Sigma Chemical Company, St. Louis, MO. Some *C. s. scutulatus* venoms were also obtained by milking Mojave rattlesnakes captured in Texas and Arizona. The localities where the snakes were captured and the $LD_{50}$ values of these venoms in mice has been published (Rael et al., 1984, *Toxicon*, 22: 980; Zepeda et al., *Comp. Biochem. Physiol.*, 81B: 319 both incorporated hereby by reference).

b. Chromatography

Mojave toxin and nontoxic phospholipase $A_2$ were isolated from *C. s. scutulatus* venom (Sigma) by DEAE-Sephadex A-50 column chromatography and preparative disc polyacrylamide gel electrophoresis. Lyophilized venom (Sigma Chemical Company, St. Louis, MO) was fractionated by DEAE-Sephadex A-50 column chromatography as described by Rael et al. (1983), *Toxicon*, 21:57, incorporated herein by reference. Subfractionation was conducted by preparative disc polyacrylamide gel electrophoresis in a Canalco 'Prep-Disc' apparatus to isolate Mojave toxin. Ten milliliters of separation gel and 5 ml of stacking gel were used. Isolation was carried out at a running pH of 9.5, a stacking pH of 8.3, a constant current of 6 mA, a flow rate of 1 ml/min and at a constant temperature of 5° C.

Separation of the acidic and basic subunits of Mojave toxin were by chromatography in a QMA anion Accel cartridge (Millipore Waters Chromatography Division, Milford, MA). The cartridge was conditioned by flushing with 5 ml of 50 mM Tris-HCl, pH 8.3, containing 2M KCl and 6M urea, the ending buffer, then with 5 ml of 50 mM Tris-HCl, pH 8.0, containing 0.1M KCl and 6M urea, the starting buffer. Five milligrams of purified Mojave toxin in starting buffer, was applied to the cartridge, then flushed with 5 ml of starting buffer to obtain the basic subunit. The acidic subunit was recovered by washing the cartridge with 5 ml of ending buffer. The fractions were dialyzed against distilled water and lyophilized.

c. Production of Antibodies

Polyclonal antisera specific for Mojave toxin and non-toxic phospholipase $A_2$ were produced in rabbits as described in Rael et al., 1984 and Zepeda et al., 1985. Monoclonal antibodies were prepared from hybridomas of NS-1 myeloma cells and spleen cells of immunized mice. The myeloma cells were obtained from The Salk Institute for Biological Studies, San Diego, CA. Sublethal doses (0.01 ug/g) of a crude Mojave toxin preparation, emulsified in Freund's complete adjuvant, were injected i.p. into BALB/c mice weekly for three weeks, then in Freund's incomplete adjuvant ten days later. Fusions were performed with polyethylene glycol (PEG 4000, GIBCO Laboratories, Grand Island, NY) three days after the last injection and then distributed into five 24-well plastic trays containing BALB/c spleen cells as a feeder layer.

During incubation, cell culture fluids were analyzed for antibodies by immunodot assay as described by Hawkes, et al., 1982, *Anal. Biochem.*, 119: 1142, (incorporated herein by reference) with a microfiltration apparatus (Bio Rad, Richmond, CA). Nitrocellulose paper containing "spots" of crude Mojave toxin preparation were incubated with culture fluids, then reacted with a peroxidase conjugated, rabbit anti-mouse IgG (Miles Laboratories, Elkhart, IN), and developed with 4-chloro-l-napthol and hydrogen peroxide. Positive cultures were expanded and cloned three times by limiting dilution. Antibody subclass was determined from culture fluids by the immunodot assay using affinity purified mouse class and subclass specific antibodies produced in rabbits (Litton Bionetics, Charleston, SC) followed by goat anti-rabbit IgG conjugated to horse raddish peroxidase (Miles Laboratories, Elkhart, IN). Ascites tumors were established by injecting stable hybridoma cells ($1 \times 10^7$) i.p. into BALB/c mice that had been primed two weeks earlier by i.p. injection of 0.5 ml pristane.

d. Electrophoresis and Immunotransfer

Electrophoresis was done in 7.5% polyacrlyamide gel slabs (PAGE) at pH 8.3. Isoelectric focusing (IEF) was done in isogel agarose (FMC Corporation, Rockland, ME) in a continuous pH gradient from 3.0 to 10.0. Standard markers (FMC Corporation, Rockland, MC) were used for pI determinations. After electrophoresis, the proteins were fixed and stained with Coomassie blue R-250 or transferred by electrophoresis to nitrocellulose sheets and the bands developed as described by Rael, et al., 1984, but using peroxidase conjugated rabbit anti-mouse IgG (Miles Laboratories, Elkhart, IN) as a secondary antibody. The substrate was 4-chloro-l-napthol and hydrogen peroxide.

e. Enzyme Assays

Phospholipase $A_2$ activity was determined by a turbidimetric method with egg yolk as substrate by the method described by Marinetti, 1965, *Biochem. Biophys. Acta*, 98:554. Egg yolk, in 0.1 M Tris-HCl buffer, pH 8.0, was adjusted so that the absorbance at 740 nm was 1.0. Venom fraction dissolved in water was added to 1.5 ml of egg yolk suspension and clearing monitored continuously in a Beckman DU 7 spectrophotometer at 740 nm. Enzyme activity was estimated from the change in absorbance between 5 and 15 min. A decrease in absorbance of 0.01 in 10 min was defined as one unit of activity.

f. Neutralization Studies

Immunoaffinity purified fractions were preincubated with antibodies for one hour at room temperature, then tested for enzyme activity and toxicity. Toxicity was determined by injecting the fraction i.p. into 15 g mice and the $LD_{50}$ determined by the Reed-Muench method (1938, *Am. J. Hygeine*, 27:493).

Monoclonal Antibody Characterization

Hybridomas secreting antibodies against Mojave toxin were established as described in section c. One clone, designated clone 12, was subcultured by limiting dilution to establish cultures derived from single cells. Fluids from nine subcultures produced antibodies reactive with identical proteins in immunoblots from electrophoresed *C. s. scutulatus* venom, purchased from Sigma Chemical Company. The antibodies were of the IgGl isotype and had a pI of 7.9, determined by IEF of purified antibodies.

The monoclonal antibodies recognized three bands in immunoblots from polyacrylamide gels and five bands within pI 5.1 and 6.1 in immunoblots from IEF gels. The specificity of the clone 12 antibodies was for the basic subunit as shown by immunoblot after IEF of the isolated Mojave toxin subunits. The monoclonal antibodies did not react with the band corresponding to non-toxic phospholipase $A_2$ present in this venom. The basic subunit focused into four bands between pI 9.3 and 9.6 and each was recognized by the clone 12 antibodies. Polyclonal antibodies against non-toxic phospholipase $A_2$ did not recognize the basic subunits of Mojave toxin showing that the two classes of phospholipases are different antigenically.

Immunoblots of venom from individual *C. s. scutulatus* snakes after IEF were developed with clone 12 antibodies to provide additional evidence for the specificity of the antibodies. Representative venoms from various Crotalus snakes from Arizona and Texas were tested for the presence of immunologically cross-reactive toxins. Multiple bands were recognized in venom from the Texas snake and the snake from southern Arizona, but none in the venom of one rattlesnake from central Arizona, a member of a population known not to have Mojave toxin in their venom. The pI's of the recognized bands were, in general, more acidic for the snakes from southern Arizona, ranging from 4.9 to 5.9, then for the recognized bands from the Texas snakes which had a pI range from 5.0 to 6.3.

EXAMPLE II

Immunoaffinity Isolation of Mojave Toxin and Related Cross-Reacting Toxin's a. Antibody Isolation Antibodies from peritoneal fluids were precipitated with ammonium sulfate, then purified by DEAE-Sephadex A-50 column chromatography. The fluids were equilibrated to starting buffer conditions (0.05 M Tris-HCl, pH 8.0, containing 0.1M KCl). The ending buffer was 0.5M Tris-HCl, pH 8.3, containing 0.3M KCl. The antibodies, which eluted with the starting buffer, were dialyzed against water and lyophilized.

b. Application to Affi-Gel

To apply the purified monoclonal antibodies to an immunoadsorbent material, the purified antibodies were rehydrated in 0.1 M MOPS buffer, pH 7.5, at a concentration of 25 mg/ml. Two milliliters of antibody solution per gm of Affi-Gel 10 (Bio-Rad, Richmond, CA), previously washed with three bed volumes of cold isopropanol and three bed volumes of distilled water, were mixed in a 50 ml test tube and rotated end over end at 4° C. for five hours. The mixture was then centrifuged and washed twice with 0.1M NaCH03, pH 7.3, containing 0.15M NaCl.

Analysis of the combined washes for protein revealed that 80% of the antibodies attached to the gel. Unreacted immunoadsorption sites were blocked by mixing the gel, end over end, with an excess of 1.0M ethanolamine-HCl for one hour at 4° C. The gel slurry was washed free of reactants with 0.05M phosphate buffer, pH 7.3, containing 0.15M NaCl.

c. Chromatography

The column was prepared by pouring five ml of gel into a 1.5 cm×5 cm column. Approximately 75 mg of *C. s. scutulatus* venom (Sigma), dissolved in the wash buffer, was added. Unbound protein was washed from the column with 0.05M phosphate buffer, pH 7.3, containing 0.1M NaCl and then with the same buffer but containing 1.0M NaCl until the spectrophotometric reading of the eluate at 280 nm was 0. The column was washed with 0.05M phosphate buffered saline, ph 7.3, then with water to release proteins bound through hydrophobic interaction. Finally, the column was washed with 0.2M acetate-HCl buffer, pH 1.8, to release all proteins attached to the antibodies. The eluted proteins were dialyzed against water and lyophilized. The column was reuseable after washing extensively with 0.05M phosphate buffered saline, pH 7.3.

d. Immunoaffinity Data

The monoclonal antibodies were conjugated to Affi-Gel and a column prepared for immunoaffinity chromatography of venom to isolate Mojave toxin. Twenty-seven percent of the venom was retained by the column after elution with buffer of which 22% was released after the column was washed with water, and 4.5% after desorption with dilute acid (Table 1). The phospholipase $A_2$ activity and the toxicity of the fraction recovered with water was higher than the fraction recovered with acid (Table 1). The difference was about 6-fold for both activities. The clone 12 antibodies neither neutralized the toxicity nor the phospholipase $A_2$ activity of either water or acid fractions at mole ratios of 5 to 1 of antibodies to toxin.

TABLE 1

Enzymatic and lethal properties of fractions from immunoaffinity chromatography of venom with clone 12 antibodies

| Eluent | Protein Recovered (mg) | Per cent Recovered | Phospho lipase (units/g)++ | $LD_{50}$ (ug/g) |
|---|---|---|---|---|
| Buffer+ | 48.0 | 73.1 | ND* | ND |
| Water | 14.7 | 22.4 | 6.64 | 0.05 |
| Acid** | 3.0 | 4.5 | 1.29 | 0.32 |
| Total | 65.7 | 100.0 | — | — |

*Not done.
+Buffer = 0.05 M phosphate buffer, pH 7.3, containing 0.1 M NaCl.
**Acid = 0.2 M acetate - HCl buffer, pH 1.8
++One unit = a decrease in adsorbance of 0.01 at 740 nm.

IEF and a corresponding immunoblot of unfractionated and chromatographed venom demonstrated one major band of pI 5.5 and one minor band of pI 5.6 developed with Coomassie blue in the fractions desorbed with water or acid. Five bands with a pI range from 5.1 to 6.1 were resolved in unfractionated venom and in the fraction desorbed with water in the immunoblot, and two bands in the fraction desorbed with acid. A small amount of Mojave toxin did not attach to the antibodies and developed in the buffer wash.

Reactivity of the monoclonal antibodies with other Crotalus venoms after IEF demonstrated the presence of cross-reactive toxin species in venom from *C. d. durissus, C. d. terrificus* from Brazil, *C. d. terrificus* from Colombia, *C. h. horridus*, and *C. v. concolor*. Venoms not recognized were from *C. adamanteus, C. atrox, C. h. atricaudatus, C. m. molassus, C. ruber, C. v. helleri, C. v. oreganus*, and *C. v. viridis*.

The preceding examples demonstrated the successful development of a hybridoma which secretes antibodies specific for the basic subunit of Mojave toxin was established. Several subclones of this clone produced antibodies of identical pI, isotype, and reactivity, criteria used to demonstrate monoclonality. A representative hybridoma has been deposited with the ATCC under the designation Css-12 (ATCC No. HB9165, deposited on Aug. 5, 1986).

As further demonstrated by the foregoing examples, the monoclonal antibodies recognized Mojave toxin, crotoxin, and cross-reacting proteins in venoms from other Crotalus species including *C. basiliscus, C. d. durissus, C. h. horridus*, and *C. v. concolor*. These cross-reacting proteins probably are also phospholytic neurotoxins.

Antibody conjugation to Affi-Gel is demonstrated to be a useful technique for isolating immunoreactive toxins from crude venom. Moreover, water was very effective in desorption of the proteins from the column, releasing over 80% of the toxin and had no effect on the biological activity of the toxin as determined by phospholipase activity and toxicity. The interaction between the toxin and the antibodies apparently was through hydrophobic bonding. The remaining 20% was retained by the column even after extensive washing with water. Desorption with acid resulted in a decrease in biological activity of the toxin, possibly from denaturation, and a reduced number of bands in IEF gels.

Analysis of individual venoms from Mojave rattlesnakes, captured in different localities, also showed a difference in pI of the Mojave toxin isoproteins. In general, venoms from *C. s. scutulatus* from west Texas, including the Big Bend region, were found to have slightly higher pI values than those from southern Arizona, showing that the populations were distinguishable by the pI of the Mojave toxin isoproteins. Venom from one particular Mojave rattlesnake captured in the vicinity of Phoenix, Arizona, did not have Mojave toxin, and the toxicity of this venom was twenty times less than venoms with the toxin. This supports other work that shows that not all individuals within a designated species possess identical, highly toxic proteins, which is reflected in the toxicity of the venom (Glenn et al., 1983). This observation may also help explain apparent discrepancies in reactivity of the monoclonal anti-Mojave toxin with venom of *C. h. horridus*, but not venom from *C. h. atricaudatus*. Most of the venoms examined were purchased from Sigma Chemical Company which were pooled samples, except some of the *C. s. scutulatus* venoms which were from individual milkings.

Monoclonal antibodies to Mojave toxin, made in accordance with the foregoing procedures, will be useful in the preparation and isolation of purified toxins from the venom of Mojave rattlesnakes and venoms containing other immunologically cross-reacting toxins. It is contemplated that such purified toxins will be particularly useful in the development of immunotoxins. Immunotoxins are antibody-toxin conjugates having specificity for tumor targets. The experimental use of such immunotoxins have generated a great degree of interest as potentially specific anti-cancer drugs. For example, the use of ricin, or the purified ricin A chain, in conjunction with antibodies, has been the subject of great interest as potentially useful reagents in tumor therapy (see, for example, Vitetta, et al., *Science* 219, 644-650 (1983); Thorpe, et al., *Immunol. Rev.* 62, 185-216 (1982)).

Procedures for deleting selected populations of cells by ricin A chain-antibody conjugates are well recognized. The antibodies of choice are those which react with antigens on tumor cells or on subsets of normal lymphocytes. By deletion of the tumor cells, it is possible, for example, to reduce tumor burdens in vivo (Krolick, et al., *J. Exp. Med.* 155, 1797 (1982)) and to remove tumor cells from bone marrow for autologous marrow transplantation (Thorpe, et al., *Nature* (London) 271, 752 (1978); and Krolick, et al., *Nature* (London 295, 604 (1982)).

By deletion of normal subsets of lymphocytes, it is possible to "up" to "down" regulate the immune response. The advantage of immunotoxins is that they are highly selective in their target cell specificity and that small doses can eliminate unwanted cells. Ricin A chain-antibody conjugates have been used primarily to delete normal and neoplastic B cells, both in vivo and in vitro. Certain laboratories have also used conjugates of ricin A chain and monoclonal antibody to eliminate neoplastic cells of T cell origin and a variety of other cancerous cells. However, ricin A chain-antibody conjugates are not active when used against certain types of tumor cells (e.g., some T cell tumors) (Neville, et al., *Immunol. Rev.* 62, 119 (1982)).

It is likely that the inability of ricin immunoconjugates, and the related immuno-conjugates to destroy tumors in certain cases is due to the requirement that these toxins be internalized by the target cell to exert their cytotoxic efforts. However, Mojave toxin, and related snake venom toxins, exert their toxic effects at the cell surface. Thus, it is proposed that particularly active immunotoxins can be developed through the coupling of such venom toxins, and in particular, Mojave toxin, to tumor specific antibodies in the manner as taught, for example, by Voisin et al. in U.S. Pat. No. 4,340,535; Jansen et al, U.S. Pat. No. 4,414,148; Neville et al. 4,359,457; or Masuho et al., U.S. Pat. No. 4,368,149, each of the foregoing patents being incorporated herein by reference. Alternatively, immunotoxins may be constructed as a means for preventing graft versus host transplantation disease as taught by Neville et al., U.S. Pat. No. 4,500,637, also incorporated herein by reference.

It is believed that the present invention and disclosure, along with the foregoing incorporated references, will provide those of skill in the art with an adequate teaching to develop such snake venom immunotoxins.

In addition to their use in the isolation of purified snake venom toxin, it is shown that monoclonal antibodies made in accordance with the present invention are useful in the detection of Mojave toxin in an aqueous sample. Such an ability to immunoreact with Mojave and related toxins indicate their utility in kits for the detection of particularly dangerous rattlesnake bites, for example, kits to distinguish between Type A and Type B bite victims. Such a kit would include a Mojave toxin monoclonal antibody in combination with an immunodetection reagent. The antibody and detection reagent may be employed in a number of different fashions as are well known in the art. For example, typical kits incorporate a variation of the well-known ELISA technique. In such kits, an enzyme-linked ligand is employed which gives a colorimetric reading proportional to the Mojave toxin concentration in the applied aqueous sample. These and other techniques suitable to the present invention include but are not limited to those described in U.S. Pat. Nos. 4,446,232 to Liotta; 4,407,943 to Cole and 4,454,233 to Wang, incorporated herein by reference.

What is claimed is:

1. A method for the isolation of biologically active snake venom toxins which are antigenically cross-reactive with Mojave toxin comprising the steps of:
   (a) preparing an immunoadsorbent material having attached thereto a monoclonal antibody to the basic subunit of Mojave toxin, the monoclonal antibody being cross reactive with an epitope present on a toxin in venom from *C. s. scutulatus, C. d. durissus, C. d. terrificus, C. h. horridus,* and *C. v. concolor,* but not cross reactive with an epitope present on a toxin in venom from *C. adamanteus, C. atrox, C. h. atricaudatus, C. m. molassus, C. ruber, C. v. helleri, C. v. oreganus,* and *C. v. viridis;*
   (b) providing a mixture which includes a snake venom having the toxin to be isolated;
   (c) contacting the material with the mixture under conditions which will promote the formation of a hydrophobic antigen/antibody complex between the antibody and the desired toxin;
   (d) washing the material to remove substances which have not complexed with the antibody using a buffer that will not disrupt the hydrophobic complex;
   (e) eluting the toxin which has complexed with the antibody under essentially non-denaturing conditions using an eluent which will disrupt the hydrophobic complex interactions between the toxin and the antibody and provide a biologically active toxin.

2. The method of claim 1 wherein the snake venom is a Crotalus venom.

3. The method of claim 2 wherein the snake venom is *C. s. scutulatus* venom.

4. The method of claim 1 wherein the snake venom is *C. d. durissus* venom.

5. The method of claim 1 wherein the snake venom is *C. d. terrificus* venom.

6. The method of claim 1 wherein the snake venom is *C. h. horridus* venom.

7. The method of claim 1 wherein the snake venom is *C. v. concolor* venom.

8. The method of claim 1, wherein the eluent is water.

9. The method of claim 1, wherein the toxin preparation has a phospholipase specific activity of at least 6 units/gram.

* * * * *